US007494220B2

United States Patent
Copland

(10) Patent No.: US 7,494,220 B2
(45) Date of Patent: Feb. 24, 2009

(54) METHOD AND SYSTEM FOR IMPROVING ACCURACY IN AUTOREFRACTION MEASUREMENTS BY INCLUDING MEASUREMENT DISTANCE BETWEEN THE PHOTORECPTORS AND THE SCATTERING LOCATION IN AN EYE

(75) Inventor: Richard James Copland, Albuquerque, NM (US)

(73) Assignee: Advanced Medical Optics, Inc., Santa Ana, CA (US)

( * ) Notice: Subject to any disclaimer, the term of this patent is extended or adjusted under 35 U.S.C. 154(b) by 1490 days.

(21) Appl. No.: 10/640,321

(22) Filed: Aug. 14, 2003

(65) Prior Publication Data

US 2004/0046935 A1 Mar. 11, 2004

Related U.S. Application Data

(63) Continuation of application No. PCT/US03/20187, filed on Jun. 27, 2003.

(60) Provisional application No. 60/403,362, filed on Aug. 15, 2002, provisional application No. 60/391,668, filed on Jun. 27, 2002.

(51) Int. Cl.
    A61B 3/00       (2006.01)
    A61B 3/02       (2006.01)

(52) U.S. Cl. .................. 351/200; 351/205; 351/222; 351/246; 600/558

(58) Field of Classification Search ............... 600/558; 351/200, 205, 222, 246
    See application file for complete search history.

(56) References Cited

OTHER PUBLICATIONS

Munnerlyn, C.R., "An Optical System for an Automatic Eye Refractor," Nov.-Dec. 1978, vol. 7, No. 6, Optical Engineering, pp. 627-630.
Cornsweet, Tom N., and Crane, Hewitt D., "Servo-Controlled Infrared Optometer," Journal of the Optical Society of America, vol. 60(4), pp. 63-69 (Apr. 1970).

*Primary Examiner*—Max Hindenburg
*Assistant Examiner*—Jonathan M Foreman

(57) ABSTRACT

A method and associated system improve accuracy in objective refraction measurements by including the measured distance between the photoreceptors of a subject's eye and the scattering location of light during the objective refraction measurements. Chromatic aberrations in the objective measurements are also compensated. The distance between the photoreceptors and the scattering location may be determined by adjusting a distance between a rotating speckled light pattern and an eye until the speckled light pattern appears to be stationary, or by employing a Scheiner disk.

50 Claims, 6 Drawing Sheets

METHOD AND SYSTEM FOR IMPROVING ACCURACY IN AUTOREFRACTION MEASUREMENTS BY INCLUDING MEASUREMENT DISTANCE BETWEEN THE PHOTORECPTORS AND THE SCATTERING LOCATION IN AN EYE

CROSS REFERENCES TO RELATED APPLICATIONS

This application is a continuation of International Patent Application No. PCT/US03/20187 filed on 27 Jun. 2003, claiming the priority benefit under 35 U.S.C. § 119(e) from U.S. Provisional Patent Application No. 60/391,668 filed on 27 Jun. 2002, and from U.S. Provisional Patent Application No. 60/403,362, filed on 15 Aug. 2002, the entirety of each of which is hereby incorporated by reference for all purposes as if fully set forth herein.

BACKGROUND AND SUMMARY OF THE INVENTION

1. Field of the Invention

This invention pertains to the field of subjective measurements and characterizations of an eye, and more particularly, to measurements and characterizations of an eye with wavefront analysis devices.

2. Description

FIG. 5 is a diagram of a human eye 500, illustrating the choroid 510, the fovea layer 520, the lens 530 and the cornea 540. The fovea layer 520 is the area of the retina that contains the densest concentration of photoreceptors.

The location of the photoreceptors in the human eye is difficult to determine accurately relative to other structures in the retina. The photoreceptors absorb visible light and they are transparent to infrared light, making an accurate measurement of their location difficult.

However, there are a number of contexts where an accurate determination of the location of the photoreceptors would prove very beneficial. In particular, as explained in more detail below, it would be beneficial to provide a system and method for accurately measuring the choroid to photoreceptor distance in the eye.

The retina requires a constant supply of blood for it to remain healthy, and in fact consumes the greatest amount of oxygen (per weight) of any tissue in the human body. Evidence from several sources show that the photoreceptor layer ranges from 0.1 mm to 0.4 mm from the choroidal blood supply in normal human eyes. The average distance between the choroid and the cones in the fovea is 0.2 mm. Although this distance has not been well studied before, it seems reasonable to suspect that in some individuals an abnormally large distance from the nourishing choroid to the photoreceptors may predispose them to visual defects resulting from sight degrading diseases such as glaucoma and diabetes. Early identification of abnormal photoreceptor to choroid spacing may result in improved patient health.

The retina is supplied with blood by two means. The inner two-thirds is nourished by branches from retinal vessels on the inner surface of the retina, while the outer one-third is nourished by the choroid. However, the fovea centralis is nourished solely by the choroid. Evidently, any overlying retinal vessels in the region of the fovea would block light from reaching the photoreceptors and would result in greatly reduced visual acuity. Since the choroid is the sole nourishment of the fovea, any abnormalities in the choroidal blood supply could result in reduced diffusion of oxygen and nutrients into the fovea and that might cause cell damage and reduced vision. While a large spacing would not normally result in visual disfunction, if the patient were to develop diabetes or glaucoma, the patient could experience an unusually rapid progress in decline of visual function. Such patients would need to be monitored more closely. Similarly, some populations, such as Native Americans, are normally more closely monitored for the onset of diabetes. It may be that data concerning choroid to photoreceptor spacing would indicate that only a small subset of those populations are actually in need of close monitoring and examination intervals could be increased for the remainder of those populations.

A second application of this measurement of the choroid to photoreceptor distance would be to improve the accuracy of objective refractive measurements that are used to determine a patient's eyeglass prescription. Many commercially available autorefractors and wavefront aberrometers reflect light off of the choroid (or the sclera) to provide a light source for such an automatic measurement. Technicians rather than highly trained doctors can perform autorefractions, and the autorefractions are faster to perform than subjective refractions.

Most people are familiar with the process of subjective refraction when an ophthalmologist flips lenses of different strengths in and out of the patient's field of view and asks the patient if a letter on the wall looks clearer or fuzzier. The repeatability of subjective refraction is generally considered to be about +/−0.25 Diopters. A few practitioners with better skill and more time to spend with the patient can achieve repeatabilities of +/−0.12 diopters.

Meanwhile, the repeatability of autorefraction measurements is better than +/−0.1 Diopters for almost all modem autorefractors, and that repeatability is much better than that of subjective refraction However, according to several review articles, about 20% of patients will have differences between a subjective refraction and an autorefraction greater than 0.5 Diopters. Significantly, repeated autorefractions performed on a particular patient from the 20% group will consistently give the same disagreement with subjective refraction, so clearly there is some kind of structural difference in those patients eyes relative to the general population.

Eyeglasses prescribed according to subjective refraction meet with greater patient satisfaction than those that would be prescribed according to autorefractors. Those patients that had more than an 0.5 Diopter discrepancy will almost always be unhappy with eyeglasses prescribed according to the autorefraction, and happy with the eyeglasses prescribed according to subjective refraction.

Accordingly, it is standard practice in the evaluation of autorefractors to consider subjective refraction to be the "gold standard" since it correlates better with patient visual experience than any other measurement. Consequently it is standard practice for ophthalmologists to fine-tune the autorefraction values by performing a subjective refraction on the patient using a phoropter. The result is that autorefractors are only used for screening purposes, or for giving an optometrist or ophthalmologist a good starting point in doing a subjective refraction.

Objective refractors use infrared light to measure the eye because infrared light reflects much more strongly out of the eye than visible light does. However, there are fundamental physical reasons to expect problems with the approach of using an infrared light beam to autorefract a patient or subject.

First, when an objective refraction measurement is performed, the light is scattered back to a measurement device from a location in the eye that is not the same as the location of the photoreceptors in the eye. That means that the above-described autorefraction measurement is referenced to a location that does not correspond to where photons are being converted into neural impulses. It has been theorized that the infrared light scatters off the choroid in the above-described autorefraction measurement, while others theorize that the light passes through the choroid and scatters off of the sclera. Regardless of the exact location at which the light scatters (hereinafter referred to as "the scattering location"), there is a definite distance between the scattering location and the photoreceptors. This phenomenon may be understood with reference to FIG. 5, which shows an infrared probe beam 25 passing into the eye 500 through the cornea 540 and lens 530, passing through the fovea 520, and striking the choroid 510. In FIG. 5, it is shown that the light scatters off the choroid 510 instead of the photoreceptors, although as explained above, the principle applies regardless of the actual scattering location.

Second, the eye works at visible wavelengths, but the infrared radiation is subject to chromatic aberration and that changes the refraction values. Fortunately, many papers have been published on the effects of chromatic aberration in the human eye. It is relatively easy to use the published data to make accurate adjustments to the refraction calculation based on published chromatic aberration values.

It is hypothesized that the significant structural difference in the 20% of patients with significant differences between subjective refraction and autorefraction is that the spacing between the photoreceptors to the scattering location is different in those patients relative to the general population. However the literature on the spacing or distance between the photoreceptors and the scattering location is much more sparse, and does not extend much past a few brief paragraphs in journals and textbooks. The effect of the chromatic aberration is such that the raw measurement will measure incorrectly by about negative 1.4 Diopters. The effect of the spacing or distance between the photoreceptors and the scattering location is such that the raw autorefractor value will be in error by about a positive 0.8 Diopters. The combined effect of the two adjustments is that the raw measurement from the autorefractor needs to be adjusted by about negative 0.6 diopters in order to agree with the subjective refraction.

Meanwhile, the Stiles-Crawford effect is also suggested as being responsible for causing discrepancies between subjective refractions and autorefractions. The Stiles-Crawford effect refers to the fact the cones in the eye show a marked preference to respond to light that is within a relatively narrow range of angles. (The fovea is where high resolution vision occurs and it is packed very densely with cones.) The effect is such that a ray of light entering the edge of a 7 mm pupil will cause a response that is about 22% as strong as a ray that enters the center of the pupil.

In normal eyes, the photoreceptors are pointed so that the peak response is pointed to somewhere in the center 1.0 mm region of the pupil. However, it can happen that the cones point toward the edge of the pupil.

One hypothesis is that the autorefractors measure inaccurately because they calculate the sphere cylinder and axis paying special attention to weight the light in the center of the pupil the most strongly. But consider the possibility that the eye is really weighting the lower half of the pupil more heavily than the center. If the sphere value in that region of the eye is one diopter different than it is in the center of the pupil, the autorefractor would read incorrectly by one diopter. Wavefront aberrometry measurements on patients can indicate how much of a difference might be caused in a subjective refraction due to a Stiles-Crawford effect.

Objective and subjective methods have been developed to evaluate the strength of the Stiles-Crawford effect, and to locate the position on the eye's pupil that is weighted the most strongly in vision. The knowledge of that location, along with a refractive power map derived from a wavefront aberration map, can be used to calculate improved values of sphere cylinder and axis that would better correspond to those that would be obtained by a subjective refraction.

One would expect that only subjects with large high order aberrations would be affected by the Stiles-Crawford effect. However, a number of subjects have been measured that have significant differences between subjective and objective refractions and they had very small high order aberrations. This observation supports the view that variations in the distance between the scattering layer and the photoreceptors is a primary reason for differences in objective and subjective refractions in those subjects, although the Stiles-Crawford effect still may play a role in some subjects.

Another factor that affects the accuracy of an autorefraction is the distance from the eye to the instrument. Autorefractors typically contain a method to assist the doctor in setting this distance to the optimal value. Many other instruments such as corneal topographers contain very accurate methods of setting that distance. One of the simplest being a camera that looks at the head from the side so that the cornea is seen in profile and the instrument moved back and forth until the apex of the cornea lines up with a reticle on a video screen.

Accordingly, it would be desirable to provide a method and system to measure the spacing or distance between the photoreceptors and the scattering location during an objective refraction measurement, and a method to use that parameter to improve the calculated spherical equivalent power on those patients. It would also be desirable to provide an instrument including an optical beampath for testing the hypothesis that the Stiles Crawford effect is responsible for the difference in autorefractions versus subjective refractions.

The present invention comprises a system and method for measuring a distance between the photoreceptors and the scattering location in an eye. Beneficially an objective refractor is employed to perform an objective refraction of the eye and to measure the distance between the photoreceptors and the scattering location in an eye. The objective refractor could be an autorefractor, a wavefront aberrometer, a photoretinoscope, or a similar device that relies on objectively measuring the eye.

In another aspect of the invention, a method for measuring a distance between the photoreceptors and the scattering location in an eye comprises performing an autorefraction of the eye with an objective refractor; focusing the eye on a rotating speckled light pattern; adjusting a distance between the speckled light pattern and the eye until the speckled light pattern appears to be stationary; measuring the distance between the speckled light pattern and the eye when the speckled light pattern appears to be stationary; and calculating the distance between the photoreceptors and the scattering location based on the distance between the speckled light pattern and the eye.

DETAILED DESCRIPTION

Figure 1:
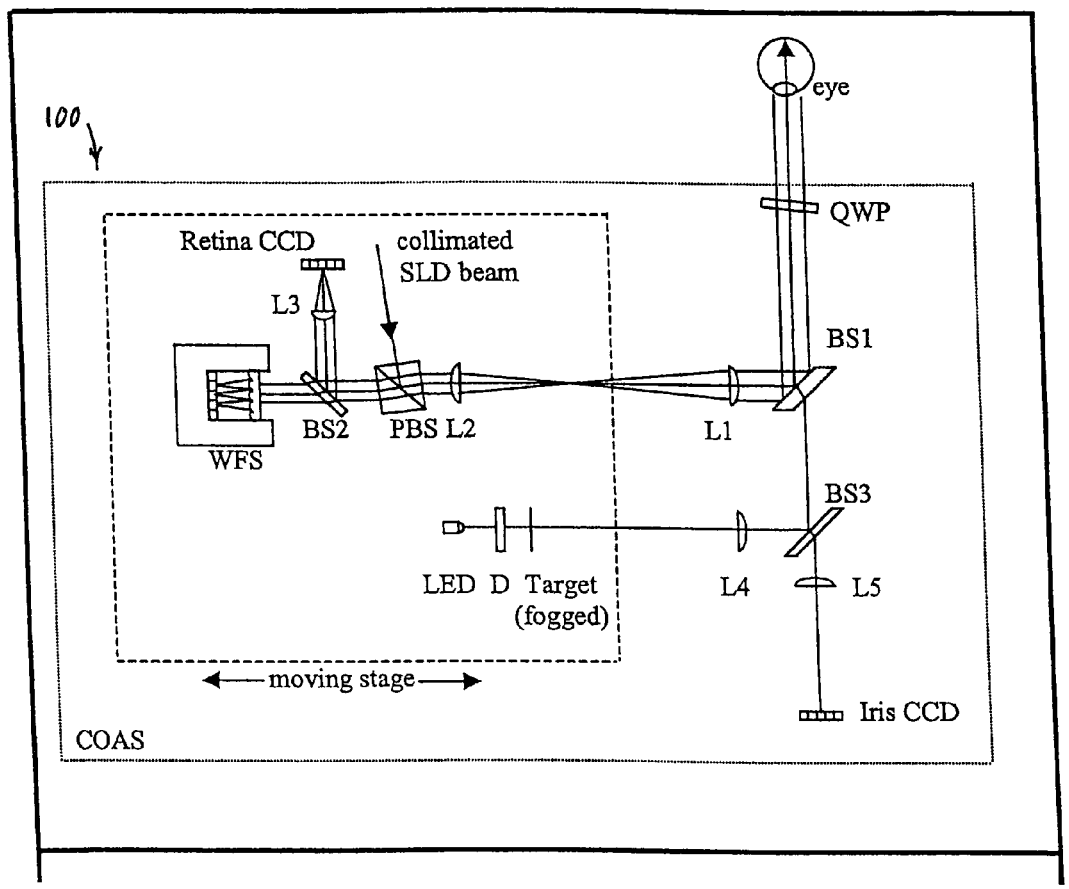
FIG. 1 shows a functional diagram of a wavefront aberrometer.

FIG. 1 shows a functional diagram of a wavefront aberrometer 100. The wavefront aberrometer 100 is a commercially successful instrument that has been used primarily by ophthalmologists for making fine adjustments to refractive laser eye surgery nomograms for treatment of myopia and astigmatism using the Lasik procedure. The wavefront aberrometer 100 can be thought of as a super-autorefractor that performs all the functions of a regular autorefractor but adds the capability to measure high order aberrations of the eye. The wavefront aberrometer 100 does this by breaking the eye into a grid with a spatial resolution of 0.2 mm spacing and measuring the optical performance of each zone. A description of a wavefront aberrometer such as the wavefront aberrometer 100 can be found in U.S. Pat. No. 6,550,917 issued on 22 Apr. 2003 in the names of Daniel R. Neal, Darrel J. Armstrong, Daniel M. Topa, and Richard J, Copland, the entirety of which is hereby incorporated herein by reference for all purposes as if fully set forth herein.

It should be understood that in lieu of the wavefront aberrometer 100, an autorefractor, a wavefront aberrometer, a photoretinoscope, or another type of objective refractor that performs objective measurements on the eye could be employed in the system and methods described below.

In the wavefront aberrometer 100, an infrared SLD beam is injected into the eye. A stage inside the wavefront aberrometer 100 moves so that the convergence of the SLD beam entering the eye is such that a small spot focuses on the retina. The subject is instructed to look at the target inside the wavefront aberrometer 100 so that the spot focuses on the fovea centralis. Light scatters in all directions from the scattering location. Some of the light scatters back through the pupil of the eye. If the lens and cornea of the eye were perfect, all the light rays exiting the pupil would be parallel and the wavefront would be planar.

Of course a real eye is not perfect so that the rays exiting the pupil are not all parallel. The wavefront sensor inside the wavefront aberrometer 100 is located at a plane that is conjugate to the cornea so that it measures the deviations from parallel of rays as they leave well-defined regions of the cornea.

The optical layout of the wavefront aberrometer 100 provides an important advantage over other similarly designed aberrometers. The wavefront sensor, collimated SLD beam and the fixation target that the subject looks at are all located on the moving stage. The result is the when the stage moves to focus the infrared beam on the retina, the wavefront sensor and the fixation target automatically move into the correct position for a good measurement. The arrangement also works well for the control of subject accommodation. Generally the stage is initialized in a position where it is in the myopic region, and the stage moves toward the hyperopic region. During this motion, the eye target will temporarily appear clear to the subject, but at that time the spot on the retinal camera will appear fuzzy. The stage automatically continues to move toward hyperopia until the SLD spot becomes well focused. At that point, the target appears fuzzy so as to keep the subjects focused as close to infinity as the eye is capable of.

A simple eye model has been developed to convert measurements from the wavefront aberrometer 100 to spherical equivalent values of a human eye. The eye model places all the refractive power in a spherical surface at the cornea, and fills the space between the "cornea" and the "fovea" with a dispersive substance that has index of refractions matching those published by Dr. Larry Thibos of the University of Indiana (e.g., Larry N. Thibos, et al., "The Chromatic Eye: a New Model of Ocular Chromatic Aberration," APPLIED OPTICS 31, 1992, 3594-3600).

Ray tracing analysis and experimental data have shown the basic validity of the equation shown below.

$$S_{vis} = P_{eff} - (V_{ir} - 1/(L+D))*(n_{vis}-1)/(n_{ir}-1), \text{ where} \quad (1)$$

$S_{vis}$ is the spherical equivalent power at the cornea that we wish to know;

$V_{ir}$ is the quantity that the wavefront aberrometer actually measures, the radius of curvature of the infrared light coming out of the cornea;

$P_{eff}$ is the effective power of the cornea and lens of the eye and is assumed to be 60;

L is the length of the eye that would result in a person having perfect vision for an assumed $P_{eff}$ (It is equal to 1/Peff. For instance, a 60 diopter cornea/lens combination would result in perfect vision if the photoreceptors were 16.6666 mm away);

D is the distance between the photoreceptors in the eye and location where the infrared light scatters ("the scattering location");

$n_{vis}$ is the average refractive index of the eye for visible light and is 1.3343 at 550 nm; and $n_{ir}$ is the average refractive index of the eye for infrared light and is 1.3247 at 840 nm.

From ophthalmology references, it is known that $P_{eff}$ ranges between 57 and 63 diopters in humans. For simplicity, it can be assumed to be 60. Performing a sensitivity analysis of the terms in the formula above, it is seen that with 63 in the equation above, the effect on the $S_{vis}$ value is only about 0.02 diopters since the relation $L=1/P_{eff}$ is contained in the equation for $S_{vis}$.

The parameters $n_{vis}$ and $n_{ir}$ are obtained from an equation that Dr. Larry Thibos published based on experimental measurements. The values he obtained are average values. Thibos' data did not extend to 840 nm, but the curve in the IR was almost flat and was very smooth so that it is appropriate to extrapolate the curve.

It is standard practice for D to be assumed to be a constant value. A value between 0.14 and 0.25 is probably used by most autorefractor software. The value is usually determined experimentally by choosing the value that gives the best fit between many subjective refractions and the autorefractor measurements. The calculated $S_{vis}$ value is very sensitive to the exact value of D. A change from 0.125 mm to 0.250 mm changes the spherical equivalent value by 0.4 Diopters.

Since the effect of the chromatic correction is about twice that due to the distance between the photoreceptors and the scattering location, it would make sense to suspect that inaccurate refractions are more related to chromatic aberration. However, analysis of data from clinical trials has indicated that applying a fixed chromatic adjustment works equally well among many different subjects. The reasoning is this: according to optical ray tracing analysis, if the refractive errors were due to an imperfect chromatic adjustment, the magnitude of the errors (expressed in diopters) should increase for subjects that are more myopic. However, that trend is not seen. Instead the range of the refraction errors is no larger for strongly myopic subjects than it is for emmetropic subjects.

Figure 2:
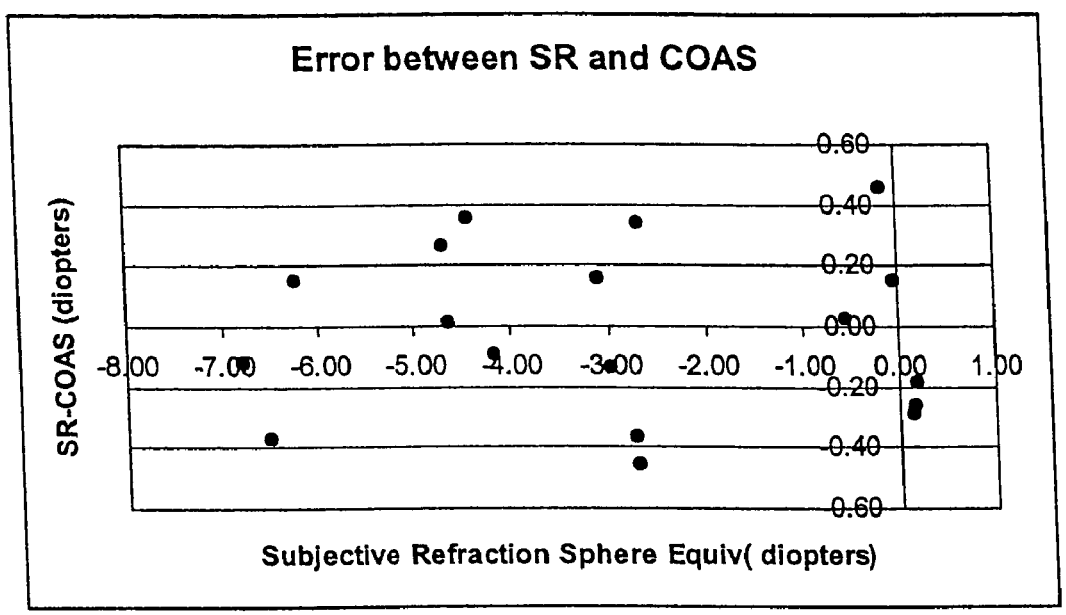
FIG. 2 shows the results of clinical trials comparing subjective refraction measurements with refractive measurements produced by a wavefront aberrometer.

That leaves the distance between the photoreceptors and the scattering location as the remaining parameter to study. According to optical ray tracing, a variation of about 0.1 mm in the distance between the photoreceptors and the scattering location would result in the same shift in the refraction error as if the subject were strongly myopic or emmetropic. In fact, this is the behavior that has been seen in clinical trials, as shown in FIG. 2.

The wavefront aberrometer 100 is designed to measure high order aberrations of the eye, which it does very well. However, it can also measure the sphere, cylinder and axis like an autorefractor.

Many ophthalmologists have observed that the wavefront aberrometer 100 obtains the same value that they get when they do a subjective refraction on themselves. However, there are a number of other ophthalmologists that have observed that the wavefront aberrometer 100 disagrees by as much as one diopter from the sphere value that they get on a subjective refraction. Some of these ophthalmologists have observed that autorefractors also always get the wrong sphere value on them.

Like most autorefractors, the wavefront aberrometer 100 also uses an infrared probe beam to perform the measurement so it is likely that the wavefront aberrometer 100 and autorefractors share a systematic bias on some subjects.

Frequently the ophthalmologist will express frustration that autorefractor accuracies are specified based on the averages over many patients. They note that a machine that is wrong on one out of five patients is nearly useless to them, regardless of how good the average value of a hundred patients is.

A recent clinical trial was performed on 20 subjects (40 eyes) to compare subjective refractions to autorefractions obtained using the wavefront aberrometer 100 and a NIDEK® ARK-2000 autorefractor. The results were consistent with the hypothesis that the distance between the photoreceptors and the scattering location ranges between 0.1 and 0.4 mm, and that range accounts for the disagreements in subjective refractions and autorefractions.

Further, the wavefront aberrometer 100 and NIDEK® instruments obtained similar measurements in those cases where the autorefractions disagreed with the subjective refractions.

The wavefront aberrometer 100 and NIDEK® instruments are different in the optical principles that they use to measure the refractions. However they are similar in that they both use an infrared probe beam. This further supports the hypothesis that the main reason for discrepancies between autorefractions and subjective refractions is that the infrared probe beam scatters at a different location than where the photoreceptors are.

Accordingly, it is desired to modify the wavefront aberrometer 100 of FIG. 1 to account for the actual location of the photoreceptors in an eye.

There are three difficulties with attempting to measure the location of the photoreceptors. The most obvious difficulty is that the photoreceptors are strongly absorbing of visible light. It is difficult for an external instrument to get a sufficiently strong reflection to locate the photoreceptors.

The second difficulty is that between the photoreceptors and the choroid there is a layer of tissue named the retinal pigment epithelium (RPE). This layer is also strongly absorbing of visible light. Its purpose is to prevent reflected visible light from scattering back into the fovea and reducing visual acuity.

The third difficulty is that the photoreceptors are transparent to infrared light. This fact was implicit in the earlier discussions that described how autorefractors work by reflecting light off of the choroid (or sclera) behind the photoreceptor layer.

Despite these difficulties, there is a relatively simple method to locate the photoreceptor layer. That is, the photoreceptor layer may be located by giving the subject a control that he can adjust until he sees some particular phenomenon occur inside the wavefront aberrometer. This has the advantage over other methods in that it involves the subject's photoreceptors in the way that they are actually used. With proper design, the task that the subject would be presented with would be much simpler than making a subjective judgement, such as judging if a projected letter is fuzzier or clearer.

The simplest task that the subject could perform would be to align two dots that he sees. In that case, the subject adjusts the convergence angle between two narrow beams until they overlap the same region of the photoreceptor layer. The adjustment has to be calibrated against the other optics in the autorefractor to make the result meaningful.

A typical embodiment of such a scheme is a Scheiner disk. It comprises a mask with two holes that is placed near a lens. A beam of light shines through the lens. At the image plane behind the lens, the beams from the two holes will overlap. The distance between the dots increases the farther an observation plane is moved farther from the focal plane.

Another task that a subject can perform, that is relatively easy to implement in hardware, is to adjust the apparent motion of a speckle pattern on a rotating speckle wheel or spinning disk.

The phenomenon of laser speckle may be unfamiliar to non-specialist in optics. (It almost certainly will be unfamiliar to patients.) Speckle is a very striking phenomenon of laser light. When a person looks at a laser beam that is illuminating a diffuse surface, such as paper or ground glass, the person will see a random collection of bright and dark spots. This phenomenon results because the wavelength of light is much smaller than the rough features on a diffuse surface. The surface acts like a sheet of randomly distributed small scattering features. The granular appearance results from constructive and destructive interference of light waves that occurs on the observer's retina. Speckle patterns can be observed if one shines a laser pointer pen at a black piece of paper. (If the laser hits a white piece of paper, the reflection is so bright that it is hard to see anything except a blur. But if you shine the laser pen across the room so the beam spreads out some, you will see the speckle patterns if you look where the beam hits the wall).

Figure 3:
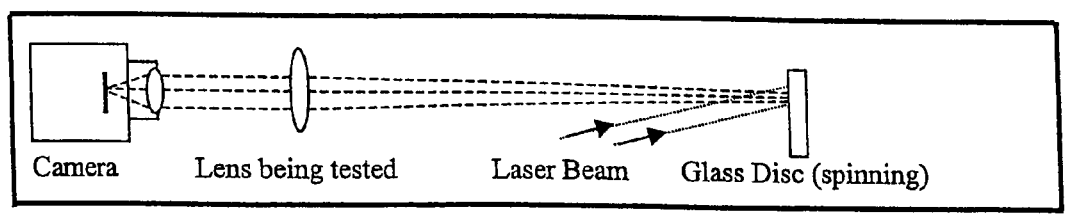
FIG. 3 shows an optical set-up to observe a rotating speckle pattern.

Speckle patterns can be used to locate the focal plane of a lens. A typical method is illustrated with respect to FIG. 3. The camera has a lens that is focused at infinity. The camera looks through the lens at the glass disc and the laser beam illuminates the glass disc from off to the side.

When the glass disc is too close to the lens, the speckle pattern will appear to a viewer to have an apparent motion in one direction. If the glass disc is too far from the lens, the apparent motion will be in the opposite direction. The speed of the apparent motion increases the farther away from focus the glass disc is located. For the special case that occurs when the glass disc is exactly at the focal point of the lens, the speckle pattern will appear not to have any net motion. Instead, the dots will appear to randomly oscillate between bright and dark while swimming around in a random manner.

Accordingly, a subject is given the task to turn a knob that changes how far the spinning glass disc, or rotating speckle wheel, is located from the lens, until it appears to the subject that the speckle pattern is stationary. In the diagram shown in FIG. 3, the CCD sensor chip corresponds to the subject's retina and the camera lens corresponds to the combined lens and cornea optical elements of the eye.

Figure 4:
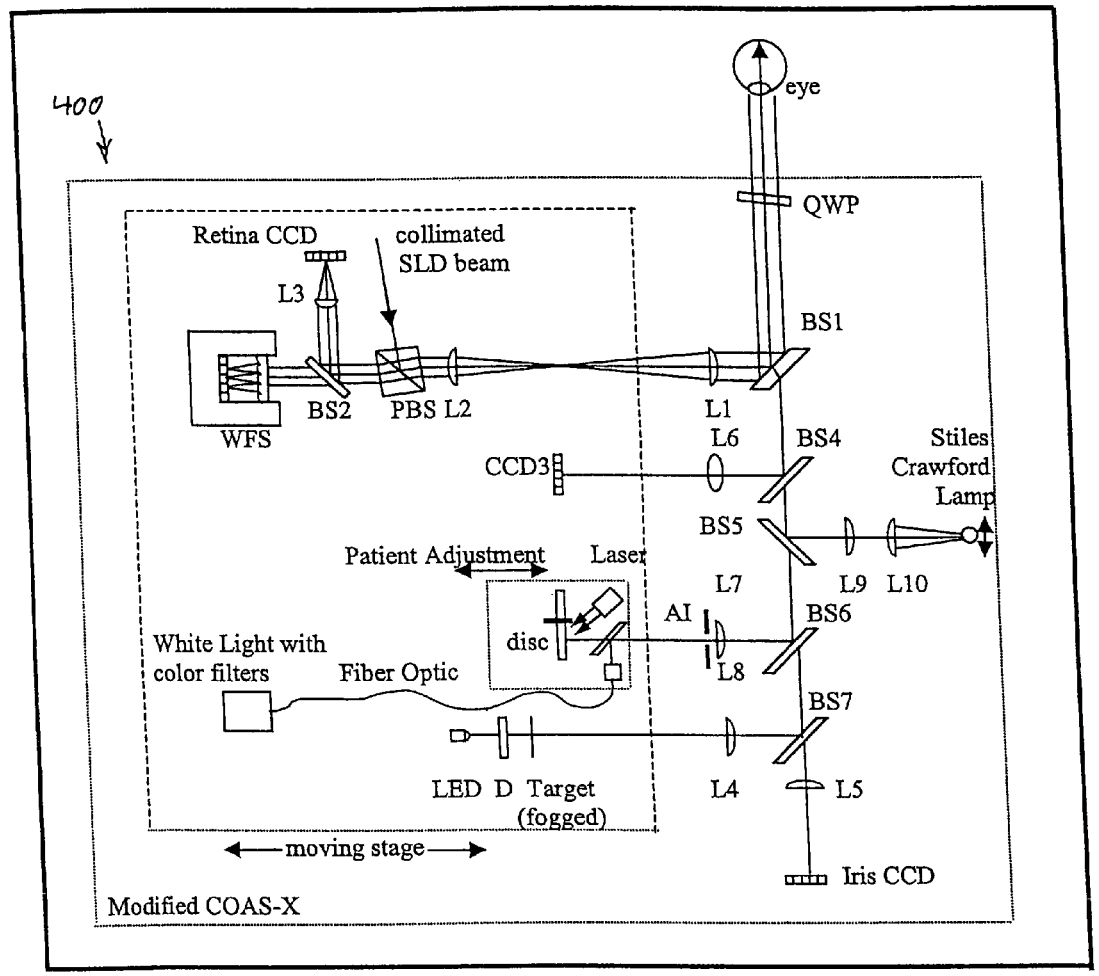
FIG. 4 shows a functional diagram of a modified wavefront aberrometer.
Figure 5:
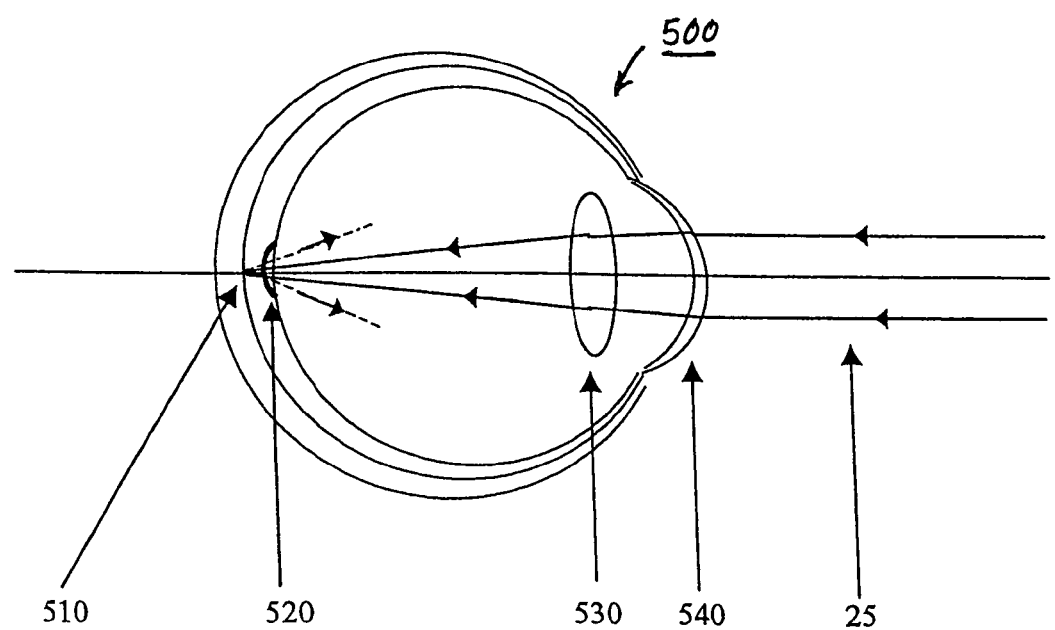
FIG. 5 illustrates several pertinent elements of a human eye.

FIG. 4 shows a modified wavefront aberrometer 400 with an additional beam.

A laser used to generate the speckle pattern is beneficially red since that color tends not to stimulate the visual accommodative response. At the same time that the subject is viewing the speckle pattern, he also sees a white crosshair pattern that is slightly fogged so that infinity focus is maintained. The speckle pattern may be continuously illuminated, or it may flash, or pulse, on and off periodically. If a red wavelength is used, the chromatic aberration of the eye will have to be considered in the calculation of the distance between the photoreceptors and the scattering location. However, if the same wavelength is used in both the wavefront sensor path and the subjective path, the calculation is more accurate as it does not include a correction for the chromatic aberration. In a particularly useful wavefront sensor according to in U.S. Pat. No. 6,550,917 as referenced above, the measurement wavelength is 840 nm, which the eye sees as a dim red color. Illumination of the speckle wheel (disk), or the Scheiner disk, can also be done at the 840 nm wavelength, but the system has to be designed so that the illumination is bright enough but is also still safe. Pulsed operation of the light source can be useful in reducing the overall light energy deposited into the eye while maintaining the subject's ability to see well enough to provide subjective input.

Speckle optometry has been used to measure the refraction of the eye. In most cases, it has been desired to measure the refractive state of the eye when it is focused at its far point. Such systems and methods typically have the subject view a target across the room through a beam splitter and a reflected image of the speckle wheel (spinning disk), that flashes on periodically. This keeps the eye focused at the far point and not at some nearer distance. A similar system may be included in the measurement of the distance between the photoreceptors and the scattering location, in that a target stimulus may appear at the far point, or at some nearer position that stimulates accommodation. However, it is not necessary to include a target stimulus for the calculation of the distance between the photoreceptors and the scattering location, since that parameter does not change depending on the accommodation of the eye. The subject can provide the subjective input by manipulating the Scheiner disk or the rotating speckle wheel (spinning disk) at any accommodative state, including an empty field, and then the objective refraction measurement can be made simultaneously, and the distance between the photoreceptors and the scattering location can be calculated from the results. Then that value can be used to improve the measurement of the objective refraction that is made at a different time, when the eye focused at it far point.

The accuracy of the calculation for improving the refraction measurement depends on how accurately the subject can provide the subjective input on when the speckle pattern appears to be stationary. The reported accuracy and repeatability of speckle optometry measurements ranges between 0.2 and 0.5 diopters. One factor that reduces the repeatability of the speckle optometry is that the eye can have astigmatism. This increases the depth of focus where the speckle pattern may appear stationary.

There are several methods that can be used to decrease the depth of focus so that a more repeatable measurement can be obtained. One method is to introduce a lens that corrects for the astigmatism of the eye. This lens can be chosen based on the objective measurement of the astigmatism, and it may be put in place automatically in the optical train.

Figure 6:
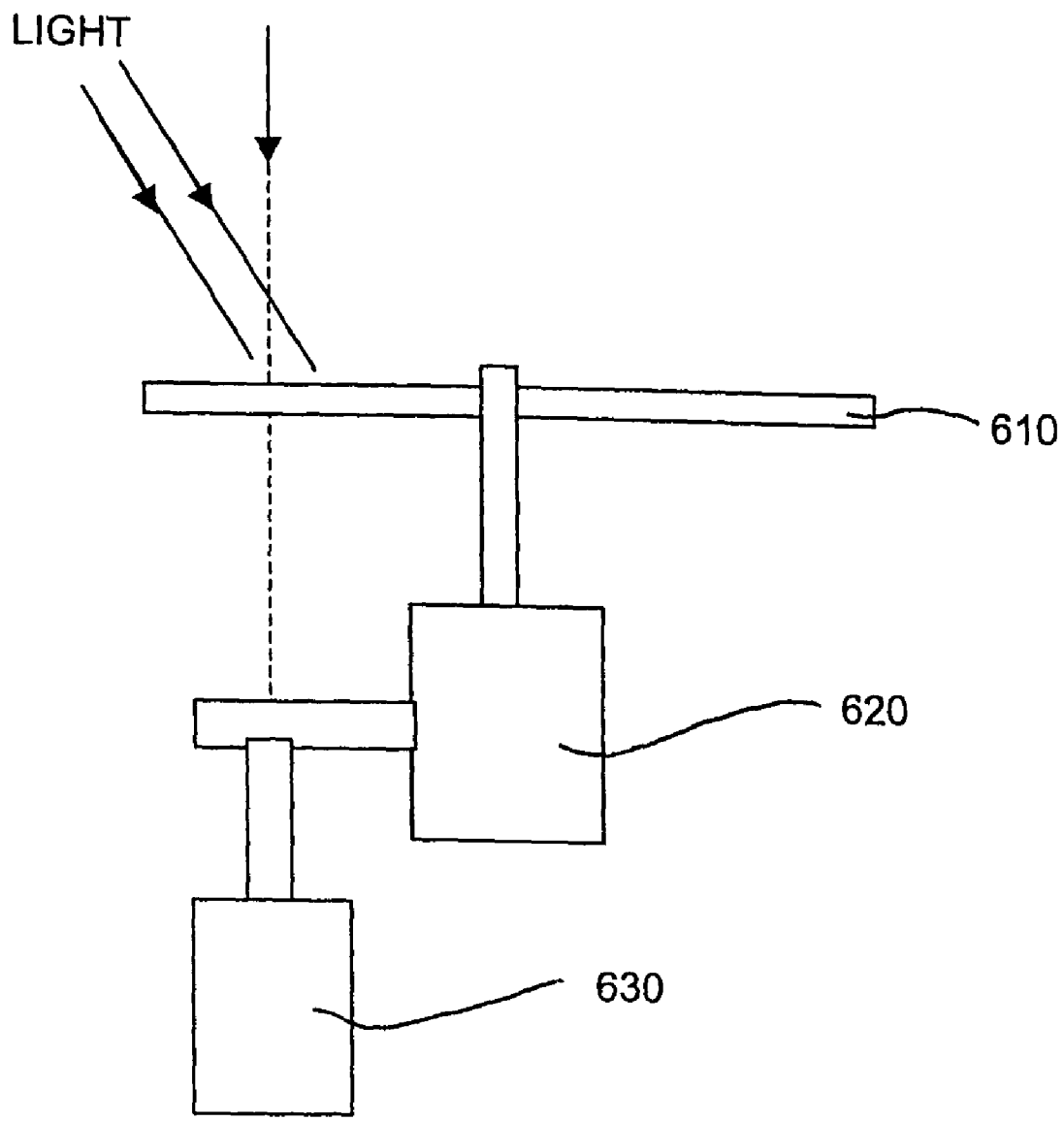
FIG. 6 illustrates a device for correcting out subject astigmatism while observing a speckle pattern on a spinning disk.

Another method that will reduce the depth of focus is to align the motion of the rotating speckle wheel (spinning disk) according to the axis of astigmatism that has been determined by the objective measurement, and this also can be done either automatically or manually. FIG. 6 illustrates a device 600 for correcting out subject astigmatism while observing a speckle pattern on a disk 610 which is being rotated by the spinning motor 620. The arrangement of FIG. 6 shows how the direction of the apparent motion of the speckles can be varied to correct for a subject's astigmatism. When the stepper motor 630 moves the disk 610 to a new stationary location, the direction of motion on the spinning disk 610 will appear to have changed to the subject. A similar arrangement for a gimbaled drum has been shown by other researchers (e.g., Henry A. Knoll, "Measuring Ametropia with a Gas Laser," American Journal of Optometry and Archives of American Academy of Optometry, July 1966, volume 43, number 7, page 415-418).

Still another method to decrease the depth of focus is called the "Method of Limits." Instead of the subject adjusting the location of the disc for stationarity, the subject adjusts the location until the speckle motion is just barely observable to move in one direction and that location is recorded. Then the subject adjusts the location of the rotating speckle wheel (spinning disk) until the speckle motion is just barely visible in the opposite direction and that location is recorded. Then the location for best stationarity is calculated as halfway in between the two recorded positions.

Yet, another method has been developed that converts the speckles into streaming lines using a spinning prism. (Hitoshi Ohzu, "The application of lasers in ophtalmology and vision research," Optica Acta, volume 26, number 8, page 1089-1101, 1979).

Spherical aberration is another factor that will increase the depth of focus where the speckle motion appears stationary. One way to decrease that effect is to optically compensate the speckle optical path for the spherical aberration of an average human eye, or to use adaptive optics to compensate for the spherical aberration of the eye that is being tested. Another method is to optically project the speckle illumination into the eye in a manner that only illuminates some small region of entrance into the eye. Such projection systems are sometimes used in fundus imaging cameras to improve the image quality by avoiding regions of the cornea that have more aberrations and these systems image an aperture stop at or near the exit pupil of the eye.

An advantage of the speckle method is that the location of the glass disc can be measured very accurately with electronic micrometers, and its location can be related mathematically by ray tracing to the location of the photoreceptors relative to the scattering location.

One of the difficulties in making any objective refraction measurement is that there are constant fluctuations in the accommodative focus of the human eye on the order of 0.5 diopters. Some researchers have theorized that these fluctuations are part of the mechanism that helps the eye maintain proper focus. Other researchers have noticed that some component of the fluctuations corresponds to the subject's heartbeat in about half of the population. The impact of the heartbeat on eye's accommodative response is unclear. However, it is clear that if an objective refraction were made at an instant that the focus is fluctuating, the measurement would disagree with a subjective refraction by the amount of the fluctuation.

Several researchers have measured these fluctuations with special autorefractors that provide a time series analysis of the eyes accommodation.

Accordingly, it is important that the wavefront aberrometer described above makes its measurements of the eye at the same time that the subject is making the judgment that the speckle pattern is stationary, or is barely moving. This can be accomplished by electronically synchronizing the measurements made by the wavefront aberrometer with a flashing light source (e.g., a pulsed laser) that illuminates the rotating speckle wheel (spinning disk), or with flashing light (e.g., a pulsed laser) that illuminates the Scheiner disk.

A drawback of the speckle method is that is has been tried before in the measurement of chromatic aberration. In that application, the deduced refractive index measurements of the eye versus wavelength disagreed with a number of different techniques of measurement of chromatic aberration of the eye that all showed fairly good agreement with each other. To confirm that the speckle method works as expected in finding the distance between the photoreceptors and the scattering location, a conventional method for measuring the chromatic aberration is also provided.

There is a subtle point concerning speckle that may have been overlooked in previous studies. According to diffraction theory, the speckle patterns are generated because light from many different directions is converging onto a photodetector. However, the Stiles-Crawford effect shows that the cones in the eye have a waveguide nature that effectively gives each cone a strongly preferred direction of light to which it will respond. The cones are only about 0.070 mm in length, so the distance from the photopigments to the front of the cones is not expected to have any significant effect on the effect on the measurement of the distance between the photoreceptors and the scattering location, but the cone directionality might. Consequently, it is important that the speckle generating system be properly designed to match the acceptance angles of the cones. The laser coherence length, the surface roughness of the spinning disk, the disk velocity, the focal length of the intermediate lens and its numerical aperture are the major variables. An adjustable iris is included at the intermediate lens in order to make the numerical aperture of the lens adjustable.

The light source for performing the chromatic aberration measurement is a white light source that has a filter wheel with 50 nm wide filters. The filtered light is coupled into an optical fiber, and the light out of the fiber is collimated by an achromatic lens. Software in the wavefront aberrometer 400 is able to move the stage until the filtered light appears to be the smallest size it can reach as it appears on a second retina camera (CCD3). The lens in front of that retina camera is compensated for the known chromatic aberrations of the eye. For this application, the compensation can be approximate since only relative retinal spot sizes are needed.

The chromatic aberration of the eye is well known, and the provision for a chromatic aberration measurement is to provide an additional diagnostic tool in the event that the speckle methodology holds some unexpected surprises.

In operation, autorefraction is performed as usual with the wavefront aberrometer 400, except that the subject is given an additional task. After the standard autorefraction is completed, the subject continues to look at the fogged target and a red laser is turned on to illuminate the spinning glass disk. The subject adjusts a knob until the speckle pattern appears to be stationary. Then the wavefront aberrometer 400 software records the location of the spinning glass disc when the subject indicates that it produces the stationary speckle pattern. The location information may be provided in terms of: (1) a distance between the speckled light pattern (or Scheiner disk) and the eye when the speckled light pattern appears to be stationary to the subject (or the two dots overlap in the case of the Scheiner disk), or (2) a distance that the speckled light pattern (or Scheiner disk) was moved from a nominal position, to the position where the speckled light pattern appears to be stationary to the subject (or the two dots overlap in the case of the Scheiner disk).

Using the well-known thin lens equation, the location information is used to calculate the distance between the photoreceptors and the scattering location, and the value used in the sphere equation that the wavefront aberrometer 400 uses when calculating the sphere, cylinder and axis for a subject.

The formula to calculate the correction to the sphere value is:

$$dP = f^2/x1 - f^2/x2, \text{ where} \qquad (2)$$

dP is the correction to the sphere value;

f is the focal length of the lens that is in between the eye and the rotating speckle wheel (spinning disk);

x1 is the distance from the lens to the rotating speckle wheel (spinning disk) for a stationary appearance of the speckle pattern for an eye that has the nominal distance between the photoreceptors and the scattering layer; and x2 is the distance from the lens to the rotating speckle wheel (spinning disk) for a stationary appearance of the speckle pattern for the eye that is being measured.

A comparison is made to determine if the use of the "customized" distance between the photoreceptors and the scattering location gives a better match of wavefront aberrometer 400 refraction to subjective refraction than the use of the average distance between the photoreceptors and the scattering location. The location of the spinning disk when the speckle pattern is stationary can be used directly to calculate the adjustment to the autorefracted sphere value. The calculation of the distance between the photoreceptors and the scattering location is an additional data reduction step that does not have to be performed if the user is only interested in the value of the sphere adjustment.

When the customized data give better results, it shows that the distance between the photoreceptors and the scattering location has been measured.

While preferred embodiments are disclosed herein, many variations are possible which remain within the concept and scope of the invention. Such variations would become clear to one of ordinary skill in the art after inspection of the specification, drawings and claims herein. The invention therefore is not to be restricted except within the spirit and scope of the appended claims.

I claim:

1. A method for improving the calculation of sphere and cylinder in an autorefraction by determining a distance between photoreceptors and a scattering location in a subject's eye, comprising:

performing an autorefraction of the eye with an objective refractor to calculate a sphere and cylinder value for the eye;

focusing the eye on a rotating speckled light pattern;

adjusting a distance between the speckled light pattern and the eye until the speckled light pattern appears to be stationary;

measuring the distance between the speckled light pattern and the eye when the speckled light pattern appears to the subject to be stationary;

calculating the distance between the photoreceptors and the scattering location based on the distance between the speckled light pattern and the eye; and adjusting the sphere and cylinder calculation to include the calculated distance between the photoreceptors and the scattering location.

2. The method of claim 1, wherein the autorefraction is performed with a wavefront aberrometer.

3. The method of claim 2, wherein the wavefront aberrometer includes an SLD light source, a fixation target, and a wavefront sensor all located on a movable platform, and wherein performing the autorefraction includes moving a position of the stage with respect to the eye.

4. The method of claim 1, further comprising producing the rotating speckled light pattern by illuminating a spinning disk with a first light source.

5. The method of claim 4, wherein the objective refractor performs the autorefraction using a second light source, and wherein the first and second light sources emit light having about a same wavelength.

6. The method of claim 4, wherein the first light source emits red light.

7. The method of claim 4, where the first light source produces illuminates the spinning disk with flashing light.

8. The method of claim 1, wherein an astigmatism of the eye is corrected for while focusing the eye on the speckled light pattern.

9. The method of claim 8, wherein the astigmatism is corrected by introducing a lens into an optical path between the eye and the speckled light pattern, wherein the lens is selected based on an astigmatism value determined by the autorefraction.

10. The method of claim 8, wherein the astigmatism is corrected by aligning a motion of the speckled light pattern to an axis of the astigmatism, where the axis of the astigmatism is determined by the autorefraction.

11. The method of claim 1, wherein a spherical aberration of the eye is at least partially corrected for while focusing the eye on the speckled light pattern.

12. The method of claim 1, further comprising measuring a chromatic aberration of the eye.

13. The method of claim 1, wherein the subject focuses on a target object while adjusting a distance between the speckled light pattern and the eye until the speckled light pattern appears to be stationary.

14. The method of claim 1, wherein the subject does not focus on any target object while adjusting a distance between the speckled light pattern and the eye until the speckled light pattern appears to be stationary.

15. A method for improving a measurement of sphere and cylinder in an autorefraction by determining the chromatic aberration of a subject's eye, comprising:

performing an autorefraction of the eye with an objective refractor to calculate a sphere and cylinder value for the eye;

focusing the eye on a rotating speckled light pattern;

adjusting a distance between the speckled light pattern and the eye until the speckled light pattern appears to the subject to be stationary when light having a first wavelength, approximately equal to the wavelength of an infrared probe beam of the objective refractor, is used to illuminate the spinning disk;

adjusting a distance between the speckled light pattern and the eye until the speckled light pattern appears to be stationary to the subject when light having a second, visible wavelength is used to illuminate the spinning disk;

measuring a difference in the locations of the spinning disk at the two wavelengths and calculating the chromatic aberration; and adjusting the sphere and cylinder calculation to include the calculated chromatic aberration.

16. The method of claim 15, wherein the autorefraction is performed with a wavefront aberrometer.

17. The method of claim 16, wherein the wavefront aberrometer includes an SLD light source, a fixation target, and a wavefront sensor all located on a movable platform, and wherein performing the autorefraction includes moving a position of the stage with respect to the eye.

18. The method of claim 15, further comprising producing the rotating speckled light pattern by illuminating a spinning disk.

19. A method for improving the measurement of sphere and cylinder in an autorefraction by determining a distance between photoreceptors and a scattering location of a subject's eye, the method comprising:

performing an autorefraction of the eye with an objective refractor to calculate a sphere and cylinder value for the eye;

providing light from a first light source through two apertures of a Scheiner disk to project two dots of light onto the subject's eye;

adjusting a distance between the first light source and the Scheiner disk until the two dots of light from the Scheiner disk appear to the subject to overlap;

measuring a distance from the first light source to the Scheiner disk when the two dots appear to the subject to overlap;

calculating the distance between the photoreceptors and the scattering location based on the distance between the first light source and the Scheiner disk when the two dots appear to the subject to overlap; and adjusting the sphere and cylinder calculation to include the measurement of the distance between the photoreceptors and the scattering location.

20. The method of claim 19, wherein the autorefraction is performed with a wavefront aberrometer.

21. The method of claim 20, wherein the wavefront aberrometer includes an SLD light source, a fixation target, and a wavefront sensor all located on a movable platform, and wherein performing the autorefraction includes moving a position of the stage with respect to the eye.

22. The method of claim 19, wherein the objective refractor performs the autorefraction using a second light source, and wherein the first and second light sources operate at about a same wavelength.

23. The method of claim 19, wherein an astigmatism of the eye is externally corrected for while projecting the two dots of light onto the subject's eye.

24. The method of claim 23, wherein the astigmatism is corrected by introducing a lens into an optical path between the eye and the speckled light pattern, wherein the lens is selected based on an astigmatism value determined by the autorefraction.

25. The method of claim 23, wherein the astigmatism is corrected by aligning a motion of the speckled light pattern to an axis of the astigmatism, where the axis of the astigmatism is determined by the autorefraction.

26. The method of claim 19, wherein a spherical aberration of the eye is at least partially corrected for while focusing the eye on the speckled light pattern.

27. The method of claim 19, further comprising measuring a chromatic aberration of the eye.

28. The method of claim 19, wherein the subject focuses on a target object while adjusting a distance between the speckled light pattern and the eye until the speckled light pattern appears to be stationary.

29. The method of claim 19, wherein the subject does not focus on any target object while adjusting a distance between the speckled light pattern and the eye until the speckled light pattern appears to be stationary.

30. A method for improving the calculation of sphere and cylinder in an autorefraction by determining a distance between photoreceptors and a scattering location in a subject's eye, comprising:
   performing an autorefraction of the eye with an objective refractor to calculate a sphere and cylinder value for the eye;
   focusing the eye on a rotating speckled light pattern produced on a spinning disk;
   adjusting a distance between the speckled light pattern and the eye by moving the spinning disk from a nominal position to a focused position where the speckled light pattern appears to the subject to be stationary;
   measuring the distance between the nominal position and the focused position where the speckled light pattern appears to the subject to be stationary; and
   adjusting the sphere and cylinder calculation to include a shift in lens power that corresponds to the measured distance between the nominal position and the focused position.

31. The method of claim 30, wherein the autorefraction is performed with a wavefront aberrometer.

32. The method of claim 31, wherein the wavefront aberrometer includes an SLD light source, a fixation target, and a wavefront sensor all located on a movable platform, and wherein performing the autorefraction includes moving a position of the stage with respect to the eye.

33. The method of claim 30, further comprising producing the rotating speckled light pattern by illuminating the spinning disk with a first laser.

34. The method of claim 33, wherein the objective refractor performs the autorefraction using a second laser, and wherein the first and second laser operate at about a same wavelength.

35. The method of claim 33, wherein the first laser emits red light.

36. The method of claim 30, wherein an astigmatism of the eye is externally corrected for while focusing the eye on the rotating speckled light pattern.

37. The method of claim 36, wherein the astigmatism is corrected by introducing a lens into an optical path between the eye and the speckled light pattern, wherein the lens is selected based on an astigmatism value determined by the autorefraction.

38. The method of claim 36, wherein the astigmatism is corrected by aligning a motion of the speckled light pattern to an axis of the astigmatism, where the axis of the astigmatism is determined by the autorefraction.

39. The method of claim 30, wherein a spherical aberration of the eye is at least partially corrected for while focusing the eye on the speckled light pattern.

40. The method of claim 30, further comprising measuring a chromatic aberration of the eye.

41. The method of claim 40, wherein a spherical aberration of the eye is at least partially corrected for while focusing the eye on the speckled light pattern.

42. A method for improving the measurement of sphere and cylinder in an autorefraction by determining a distance between photoreceptors and a scattering location of a subject's eye, the method comprising:
   performing an autorefraction of the eye with an objective refractor to calculate a sphere and cylinder value for the eye;
   providing light from a first light source through two apertures of a Scheiner disk to project two dots of light onto the subject's eye;
   adjusting a distance between the light source and the Scheiner disk by moving the light source from a nominal position to a focused position where the two dots appear to the subject to overlap;
   measuring the distance between the nominal position and the focused position where the two dots appear to the subject to overlap; and
   adjusting the sphere and cylinder calculation to include a shift in lens power that corresponds to the measured distance between the nominal position and the focused position.

43. The method of claim 42, wherein the autorefraction is performed with a wavefront aberrometer.

44. The method of claim 43, wherein the wavefront aberrometer includes an SLD light source, a fixation target, and a wavefront sensor all located on a movable platform, and wherein performing the autorefraction includes moving a position of the stage with respect to the eye.

45. The method of claim 42, further comprising producing two dots with a first light source.

46. The method of claim 45, wherein the objective refractor performs the autorefraction using a second light source, and wherein the first and second light sources operate at about a same wavelength.

47. The method of claim 42, wherein an astigmatism of the eye is externally corrected for while focusing the eye on the two dots of light.

48. The method of claim 47, wherein the astigmatism is corrected by introducing a lens into an optical path between the eye and the speckled light pattern, wherein the lens is selected based on an astigmatism value determined by the autorefraction.

49. The method of claim 47, wherein the astigmatism is corrected by aligning a motion of the speckled light pattern to an axis of the astigmatism, where the axis of the astigmatism is determined by the autorefraction.

50. The method of claim 42, further comprising measuring a chromatic aberration of the eye.

* * * * *